(12) United States Patent
Yang et al.

(10) Patent No.: US 9,655,111 B2
(45) Date of Patent: May 16, 2017

(54) METHOD FOR TRANSMITTING DATA, METHOD FOR RECEIVING DATA, AND DEVICE

(71) Applicant: Huawei Technologies Co., Ltd., Shenzhen (CN)

(72) Inventors: Xun Yang, Shenzhen (CN); Mu Zhao, Shenzhen (CN); Yanping Jiang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 196 days.

(21) Appl. No.: 14/677,263

(22) Filed: Apr. 2, 2015

(65) Prior Publication Data

US 2015/0230247 A1    Aug. 13, 2015

Related U.S. Application Data

(63) Continuation of application No. PCT/CN2013/073641, filed on Apr. 2, 2013.

(30) Foreign Application Priority Data

Oct. 15, 2012    (CN) .......................... 2012 1 0390078

(51) Int. Cl.
*H04W 72/04* (2009.01)
*H04W 8/20* (2009.01)
(Continued)

(52) U.S. Cl.
CPC ....... *H04W 72/0446* (2013.01); *H04L 1/1854* (2013.01); *H04L 5/0055* (2013.01);
(Continued)

(58) Field of Classification Search
None
See application file for complete search history.

(56) References Cited

U.S. PATENT DOCUMENTS

2004/0037291 A1    2/2004 Attar et al.
2004/0214582 A1    10/2004 Lan et al.
(Continued)

FOREIGN PATENT DOCUMENTS

CN    1728838 A    2/2006
CN    1825780 A    8/2006
(Continued)

*Primary Examiner* — Min Jung
(74) *Attorney, Agent, or Firm* — Leydig, Voit & Mayer, Ltd.

(57) ABSTRACT

The present invention provides a method for transmitting data, a method for receiving data and a device. The transmitting method includes: transmitting, by an STA, characterizing information to an AP, the characterizing information is used to characterize a maximum transmission delay allowed by uplink data to be transmitted by the STA; receiving, by the STA, transmission time that is specified for the STA and returned by the AP within the maximum transmission delay allowed by the uplink data to be transmitted by the STA, wherein the transmission time is within a range of the maximum transmission delay allowed by the uplink data to be transmitted by the STA; and transmitting, by the STA, the uplink data to the AP within the transmission time. Technical solutions of the present invention solve a problem of data transmission in an emergency application scenario, and guarantee requirements placed by emergency data upon transmission delay.

25 Claims, 5 Drawing Sheets

(51) Int. Cl.
*H04L 5/00* (2006.01)
*H04W 4/22* (2009.01)
*H04W 72/12* (2009.01)
*H04L 1/18* (2006.01)
*H04W 84/12* (2009.01)
*A61B 5/00* (2006.01)
*H04W 56/00* (2009.01)

(52) U.S. Cl.
CPC ............... *H04W 4/22* (2013.01); *H04W 8/20* (2013.01); *H04W 72/048* (2013.01); *H04W 72/0413* (2013.01); *H04W 72/1236* (2013.01); *A61B 5/0002* (2013.01); *H04W 56/00* (2013.01); *H04W 84/12* (2013.01)

(56) References Cited

U.S. PATENT DOCUMENTS

| | | | |
|---|---|---|---|
| 2005/0026621 A1* | 2/2005 | Febvre | H04B 7/18539 455/450 |
| 2006/0023629 A1 | 2/2006 | Kim et al. | |
| 2007/0025357 A1* | 2/2007 | Zhang | H04L 1/0018 370/395.4 |
| 2007/0195789 A1 | 8/2007 | Yao | |
| 2009/0196275 A1* | 8/2009 | Damnjanovic | H04W 28/06 370/345 |
| 2009/0279509 A1 | 11/2009 | Reumerman et al. | |
| 2010/0297979 A1* | 11/2010 | Watfa | H04W 8/205 455/404.1 |
| 2011/0085522 A1 | 4/2011 | Park et al. | |
| 2011/0151914 A1 | 6/2011 | Leng et al. | |
| 2011/0158206 A1 | 6/2011 | Shrestha et al. | |
| 2012/0082036 A1 | 4/2012 | Abedi et al. | |
| 2012/0236760 A1* | 9/2012 | Ionescu | H04W 4/22 370/259 |
| 2013/0303104 A1* | 11/2013 | Venkatachalam | H04W 76/048 455/404.1 |

FOREIGN PATENT DOCUMENTS

| | | |
|---|---|---|
| CN | 102014340 A | 4/2011 |
| CN | 102017749 A | 4/2011 |
| CN | 2011155256 A1 | 12/2011 |
| CN | 102342170 A | 2/2012 |
| EP | 2445236 A1 | 4/2012 |
| WO | WO 2010067396 A1 | 6/2010 |
| WO | WO 2011155256 A1 | 12/2011 |

* cited by examiner

METHOD FOR TRANSMITTING DATA, METHOD FOR RECEIVING DATA, AND DEVICE

CROSS-REFERENCE TO RELATED APPLICATIONS

This application is a continuation of International Patent Application No. PCT/CN2013/073641, filed on Apr. 2, 2013, which claims priority to Chinese Patent Application No. 201210390078.X, filed on Oct. 15, 2012, both of which are hereby incorporated by reference in their entireties.

TECHNICAL FIELD

The present invention relates to communication technologies and, in particular, to a method for transmitting data, a method for receiving data, and a device.

BACKGROUND

In an application scenario of 802.11ah, 6000 sensor stations (Station, STA for short) are supported at most. These STAs are generally some intelligent meter-reading devices, which, for instance, may be a device for reading a water meter, an electricity meter, a gas meter, etc. The STAs need to upload data to a remote control device such as a radio access point (Access Point, AP for short). Currently, there are two application requirements for an STA to upload data to an AP, an active upload requirement and a passive upload requirement, respectively.

At present, no matter for the active upload requirement or the passive upload requirement, some methods are provided, which enable the STA to get access to a channel and thus transmit data to the AP. In 802.11 ah, there are some emergency application scenarios such as a telemedicine application scenario. In these emergency application scenarios, it is required that data of the STA can be transmitted to the AP timely, but in the current methods, the access of the STA to the AP may need a long time waiting, which cannot meet requirements placed by emergency data upon transmission delay in the emergency scenarios.

SUMMARY

Embodiments of the present invention provide a method for transmitting data, a method for receiving data and a device, which are used to solve a problem of data transmission in an emergency application scenario, and guarantee requirements placed by emergency data upon transmission delay.

In a first aspect, a method for transmitting data is provided, including:

transmitting, by a station STA, characterizing information to a radio access point AP, wherein the characterizing information is used to characterize a maximum transmission delay allowed by uplink data to be transmitted by the STA;

receiving, by the STA, transmission time that is specified for the STA and returned by the AP within the maximum transmission delay allowed by the uplink data to be transmitted by the STA, wherein the transmission time is within a range of the maximum transmission delay allowed by the uplink data to be transmitted by the STA; and transmitting, by the STA, the uplink data to the AP within the transmission time.

In a second aspect, a method for receiving data is provided, including:

receiving, by a radio access point AP, characterizing information transmitted by a station STA, where the characterizing information is used to characterize a maximum transmission delay allowed by uplink data to be transmitted by the STA;

returning, by the AP, transmission time that is specified for the STA to the STA within the maximum transmission delay allowed by the uplink data to be transmitted by the STA, wherein the transmission time is within a range of the maximum transmission delay allowed by the uplink data to be transmitted by the STA; and receiving, by the AP, the uplink data transmitted by the STA within the transmission time.

In a third aspect, a station STA is provided, including:

a first transmitting module, configured to transmit characterizing information to a radio access point AP, wherein the characterizing information is used to characterize a maximum transmission delay allowed by uplink data to be transmitted by the STA;

a first receiving module, configured to receive transmission time that is specified for the STA and returned by the AP within the maximum transmission delay allowed by the uplink data to be transmitted by the STA, wherein the transmission time is within a range of the maximum transmission delay allowed by the uplink data to be transmitted by the STA; and a second transmitting module, configured to transmit the uplink data to the AP within the transmission time.

In a fourth aspect, a radio access point AP is provided, including:

a first receiving module, configured to receive characterizing information transmitted by a station STA, wherein the characterizing information is used to characterize a maximum transmission delay allowed by uplink data to be transmitted by the STA;

a first transmitting module, configured to return transmission time that is specified for the STA to the STA within the maximum transmission delay allowed by the uplink data to be transmitted by the STA, wherein the transmission time is within a range of the maximum transmission delay allowed by the uplink data to be transmitted by the STA; and a second receiving module, configured to receive the uplink data transmitted by the STA within the transmission time.

According to the method for transmitting data and the station STA provided by embodiments of the present invention, the STA informs an AP that uplink data to be transmitted belong to emergency data by transmitting characterizing information that characterizes a maximum transmission delay allowed by the uplink data to be transmitted by the STA to the AP, so that the AP returns transmission time that is specified for the STA within a range of the maximum transmission delay to the STA within the maximum transmission delay, after receiving the transmission time specified by the AP for the STA within the range of the maximum transmission delay, the STA transmits the uplink data to the AP within the transmission time, so that the uplink data are transmitted to the AP within the maximum transmission delay as far as possible, which is particularly applicable to data transmission in an emergency application scenario, and helps to guarantee requirements placed by emergency data upon the transmission delay.

According to the method for receiving data and the radio access point AP provided by embodiments of the present invention, the AP receives characterizing information transmitted by an STA, wherein the characterizing information characterizes a maximum transmission delay allowed by uplink data to be transmitted by the STA, then the AP returns transmission time that is specified for the STA within a range of the maximum transmission delay to the STA within the maximum transmission delay characterized by the characterizing information, and then receives the uplink data transmitted by the STA within the transmission time, so that the uplink data of the STA are transmitted within the maximum transmission delay as far as possible, which is particularly applicable to data transmission in an emergency application scenario, and helps to guarantee requirements placed by emergency data upon the transmission delay.

BRIEF DESCRIPTION OF DRAWINGS

In order to make technical solutions in embodiments of the present invention or the prior art clearer, accompanying drawings used in the description of the embodiments or the prior art will be briefly described hereunder. Obviously, the described drawings are merely some embodiments of present invention. For persons skilled in the art, other drawings may be obtained based on these drawings without any creative effort.

DESCRIPTION OF EMBODIMENTS

In order to make objectives, technical solutions, and advantages of embodiments of the present invention clearer, the technical solutions in embodiments of the present invention are hereinafter described clearly and completely with reference to accompanying drawings in embodiments of the present invention. Obviously, the described embodiments are only a part of embodiments of the present invention, rather than all embodiments of the present invention. All other embodiments obtained by persons of ordinary skill in the art based on embodiments of the present invention without any creative efforts shall fall within the protection scope of the present invention.

Figure 1:
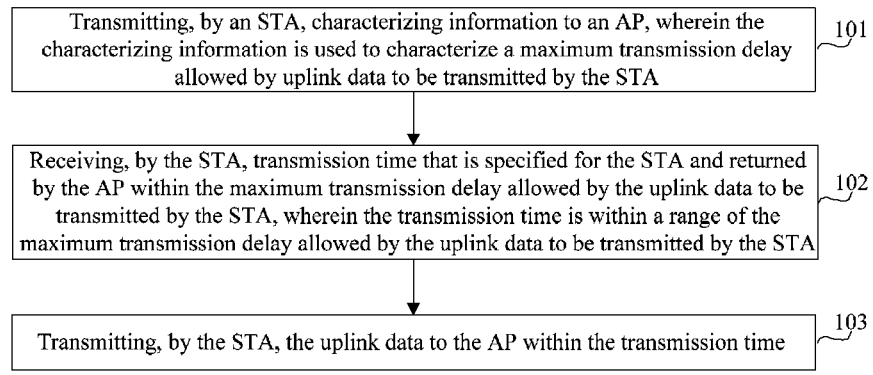
FIG. 1 is a flow chart of a method for transmitting data according to an embodiment of the present invention.

FIG. 1 is a flow chart of a method for transmitting data according to an embodiment of the present invention. As shown in FIG. 1, the method of this embodiment includes:

Step 101, transmitting, by an STA, characterizing information to an AP, wherein the characterizing information is used to characterize a maximum transmission delay allowed by uplink data to be transmitted by the STA.

As an executive body of this embodiment, the STA may be any STA in a scenario of 802.11, and especially may be an STA having emergency data that need to be transmitted to the AP. The STA having the emergency data that need to be transmitted to the AP is described illustratively: for instance, in a telemedicine application scenario, the patients are usually some elderly persons in need of care, they will carry the STA with themselves, the STA reports some sign information at regular time, for instance, heart rate, blood pressure, respiration, and body temperature of the patients; when some emergency situations occur, for instance, when the heart rate of the patient exceeds or is less than a certain value, the STA will turn into an intensive monitoring state, data monitored by the STA need to be uploaded to the AP at a relatively short time, if a delay occurs, severe consequences may be generated, that is, the STA in this case is the STA having the emergency data that need to be transmitted to the AP. For another example, in some environmental monitoring scenario, when there are data triggered by an emergency event, which need to be reported by an STA, the STA at this time also belongs to the STA having the emergency data that need to be transmitted to the AP.

Firstly, when the STA is about to transmit uplink data to the AP, if they are emergency data, characterizing information that characterizes a maximum transmission delay allowed by the uplink data to be transmitted to can be transmitted to the AP firstly, the AP may learn that the uplink data to be transmitted by the STA are relatively urgent via the maximum transmission delay characterized by the characterizing information, based on this, the AP will schedule the STA promptly, so that the STA can transmit the uplink data to the AP within the maximum transmission delay allowed by the uplink data to be transmitted. In this embodiment, the characterizing information transmitted by the STA to the AP not only can characterize the maximum transmission delay allowed by the uplink data to be transmitted by the STA, meanwhile, but also may characterize whether the uplink data to be transmitted by the STA are emergency data and a degree of emergency thereof.

In this embodiment, the maximum transmission delay allowed by the uplink data to be transmitted by the STA actually refers to a period of time after the STA starts to transmit the characterizing information to the AP, and the STA needs to complete transmission of the uplink data to be transmitted during this period of time.

Step 102, receiving, by the STA, transmission time that is specified for the STA and returned by the AP within the maximum transmission delay allowed by the uplink data to be transmitted by the STA, wherein the transmission time is within a range of the maximum transmission delay allowed by the uplink data to be transmitted by the STA.

After receiving the characterizing information transmitted by the STA, the AP may learn the maximum transmission delay allowed by the uplink data to be transmitted by the STA according to the characterizing information. In order to enable the STA to transmit the uplink data to the AP within the maximum transmission delay allowed by the uplink data to be transmitted, the AP specifies for the STA transmission time within the range of the maximum transmission delay allowed by the uplink data to be transmitted by the STA within the maximum transmission delay allowed by the uplink data to be transmitted by the STA, and transmits the transmission time specified for the STA to the STA within the maximum transmission delay allowed by the uplink data to be transmitted by the STA. The transmission time specified by the AP for the STA may be a time point, and may also be a time window (i.e. a short time). Correspondingly, the STA receives the transmission time returned by the AP within the maximum transmission delay allowed by the uplink data to be transmitted by the STA.

Step 103, transmitting, by the STA, the uplink data to the AP within the transmission time.

After receiving the transmission time returned by the AP, the STA transmits the uplink data to the AP within the transmission time. Specifically, the STA competes for a channel to get access to the AP within the transmission time, and thus transmits the uplink data to the AP within the maximum transmission delay allowed by the uplink data to be transmitted.

As seen above, in the method for transmitting data provided by this embodiment, an STA informs an AP that uplink data to be transmitted belong to emergency data by transmitting characterizing information that characterizes a maximum transmission delay allowed by the uplink data to be transmitted by the STA to the AP, so that the AP returns transmission time that is specified for the STA within a range of the maximum transmission delay to the STA within the maximum transmission delay, after receiving the transmission time specified by the AP for the STA within the range of the maximum transmission delay, the STA transmits the uplink data to the AP within the transmission time, so that the uplink data are transmitted to the AP within the maximum transmission delay as far as possible, which is particularly applicable to data transmission in an emergency application scenario, and helps to guarantee requirements placed by emergency data upon the transmission delay.

In an optional implementation, step 101, i.e. a way for the STA to transmit the characterizing information to the AP includes but is not limited to the followings:

Transmitting, by the STA, a first added control frame to the AP, wherein the first added control frame includes the characterizing information. Specifically, the STA carries the characterizing information via the added control frame to transmit the same to the AP. In order to facilitate a distinction from other added control frames, the added control frame carrying the characterizing information is referred to as the first added control frame herein.

Transmitting, by the STA, a first added management frame to the AP, wherein the first added management frame includes the characterizing information. Specifically, the STA carries the characterizing information via the added management frame to transmit the same to the AP. In order to facilitate a distinction from other added management frames, the added management frame carrying the characterizing information is referred to as the first added management frame herein.

Transmitting, by the STA, a first extended control frame to the AP, wherein the first extended control frame includes the characterizing information. Specifically, the STA carries the characterizing information via the extended control frame by extending the existing control frame to transmit the same to the AP. For instance, the extended control frame herein may be an existing ps-poll frame A manner for extending the control frame may be adding a field or an information element (Information Element, IE for short) in the control frame to carry the characterizing information via the added field or the IE. In order to facilitate a distinction from other extended control frames, the extended control frame carrying the characterizing information is referred to as the first extended control frame herein.

Transmitting, by the STA, a first extended management frame to the AP, wherein the first added management frame includes the characterizing information. Specifically, the STA carries the characterizing information via the extended management frame by extending the existing management frame to transmit the same to the AP. For instance, the extended management frame herein may be an existing association frame or reassociation frame. A manner for extending the management frame may be adding a field or an IE in the management frame to carry the characterizing information via the added field or the IE. In order to facilitate a distinction from other extended management frames, the extended management frame carrying the characterizing information is referred to as the first extended management frame herein.

Transmitting, by the STA, a first extended data frame to the AP, wherein the first extended data frame includes the characterizing information. Specifically, the STA carries the characterizing information via the extended data frame by extending the existing data frame to transmit the same to the AP. For instance, the extended data frame herein may be a data frame used by the STA for transmitting current uplink data to the AP, and characterizing data corresponding to uplink data to be transmitted next time are carried in the data frame transmitting the current uplink data A manner for extending the data frame may be adding a field or an IE in the data frame to carry the characterizing information via the added field or the IE. In order to facilitate a distinction from other extended data frames, the extended data frame carrying the characterizing information is referred to as the first extended data frame herein.

In an optional implementation, step 102, i.e. an implementation for the STA to receive the transmission time that is specified for the STA and returned by the AP within the maximum transmission delay allowed by the uplink data to be transmitted by the STA includes: receiving, by the STA, a first acknowledgement response (ACK) transmitted by the AP within the maximum transmission delay allowed by the uplink data to be transmitted by the STA, wherein the first acknowledgement response includes the specified time. Specifically, after receiving the characterizing information transmitted by the STA, the AP returns an ACK frame to the STA, and the transmission time that is specified for the STA is carried via the ACK frame.

It should be noted herein that, in this implementation, the STA may employ any one of manners provided in the optional implementation of step 101 described above to transmit the characterizing information to the AP.

In an optional implementation, step 102, i.e. another implementation for the STA to receive the transmission time that is specified for the STA and returned by the AP within the maximum transmission delay allowed by the uplink data to be transmitted by the STA may include: receiving, by the STA, a beacon frame (Beacon) transmitted by the AP within the maximum transmission delay allowed by the uplink data to be transmitted by the STA, wherein the beacon frame includes an identifier of the STA and the specified time. Specifically, after receiving the characterizing information transmitted by the STA, the AP transmits the beacon frame to the STA, and the transmission time that is specified for the STA is carried via the beacon frame. It is required herein that a transmission interval of the beacon frame should end within the range of the maximum transmission delay allowed by the uplink data to be transmitted by the STA.

It should be noted herein that, in this implementation, the STA may employ any one of manners provided in the optional implementation of step 101 described above to transmit the characterizing information to the AP.

Optionally, in this implementation, if the AP receives characterizing information transmitted respectively by a plurality of STAs within a period of time, then the AP may specify corresponding transmission time for each STA according to maximum transmission delay characterized by the characterizing information transmitted by each STA, and then transmits the transmission time respectively corresponding to the plurality of STAs to the plurality of STAs via a same beacon frame; in addition, in order to characterize which STAs need to receive the beacon frame, the AP carries the identifier of the STA corresponding to each transmission time in the beacon frame simultaneously, that is to say, in addition to an identifier of an STA which is regarded as the executive body of this embodiment and transmission time specified by the AP for the STA, the beacon frame may also include: identifiers of other STAs besides the STA and the transmission time that is specified by the AP for the other STAs within a range of the maximum transmission delay allowed by the uplink data to be transmitted by the other STAs.

Wherein, the identifier of the STA may be any information that may uniquely identify the STA, for instance, may be a media access control (Media Access Control, MAC for short) address of the STA or an association identifier (Association ID, AID for short) of the STA.

It should be noted herein that, in a case where the AP receives characterizing information transmitted by a plurality of STAs within a period of time, the AP may specify same transmission time for the plurality of STAs or specify different transmission time for the plurality of STAs according to size of the maximum transmission delay characterized by the characterizing information transmitted by the plurality of STAs respectively. In addition, if the transmission time specified by the AP for each STA is a time window (i.e. a short time), then time windows specified by the AP for respective STAs may be overlapped. Moreover, in addition to a time window, the transmission time specified by the AP for each STA may also be a specific time point. It will be appreciated herein that: the AP may specify the transmission time for each STA independently, and may also specify the transmission time for each STA with an overall consideration of the maximum transmission delay characterized by the characterizing data transmitted by a plurality of STAs, so as to guarantee that not only uplink data can be transmitted by each STA within the time as required, but also the utilization of time resources can be improved.

Based on the descriptions above, in an optional implementation, the characterizing information may be the maximum transmission delay allowed by the uplink data to be transmitted by the STA. The STA may support maximum transmission delays allowed by different uplink data being different by means of directly transmitting the characterizing information that characterizes the maximum transmission delay allowed by the uplink data to be transmitted to the AP, which has strong flexibility and adaptability.

Figure 2:
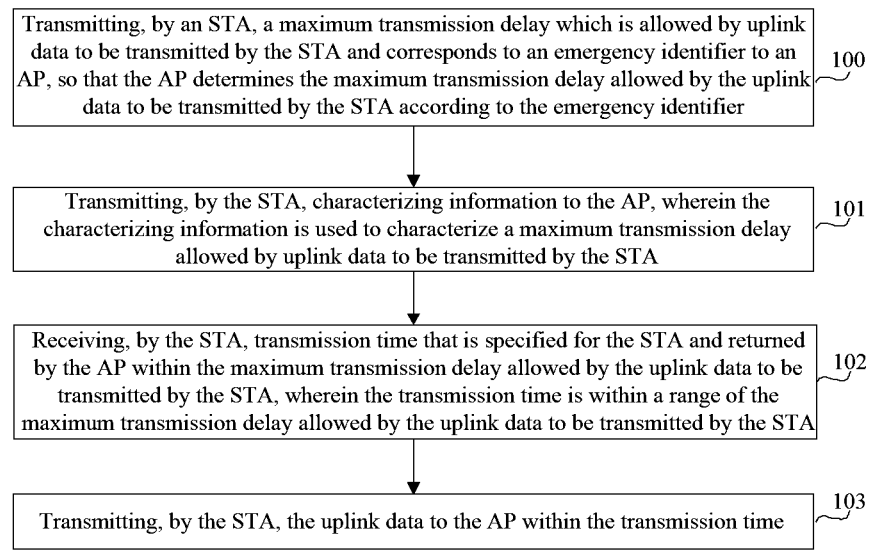
FIG. 2 is a flow chart of a method for transmitting data according to another embodiment of the present invention.

In an implementation, the characterizing information may be an emergency identifier that identifies the uplink data to be transmitted by the STA as emergency data. For instance, the emergency identifier may use a bit to represent. Based on this, as shown in FIG. 2, the method of this embodiment before step 101 includes:

Step 100, transmitting, by an STA, a maximum transmission delay which is allowed by uplink data to be transmitted by the STA and corresponds to an emergency identifier to an AP, so that the AP determines the maximum transmission delay allowed by the uplink data to be transmitted by the STA according to the emergency identifier.

In this implementation, the STA transmits the maximum transmission delay allowed by emergency data on the STA to the AP in advance, and then only needs to transmit the emergency identifier to the AP before needing to transmit the emergency data. In this case, the maximum transmission delay allowed by the emergency data which has been transmitted by the STA before can be stored on the AP in advance, then, after receiving the emergency identifier transmitted by the STA, the uplink data to be transmitted by the STA may be determined as the emergency data, and the maximum transmission delay allowed by the uplink data to be transmitted by the STA may be determined. For the AP, there will be a plurality of STAs getting access to the AP generally, maximum transmission delays allowed by emergency data on respective STAs may be different, thus the AP needs to maintain a corresponding relation between a maximum transmission delay allowed by the emergency data on each STA and an emergency identifier transmitted by the STA, implementations of the corresponding relation will not be limited, and all manners that may be implemented by the AP are applicable to the this embodiment.

Step 100, i.e. a way for the STA to transmit the maximum transmission delay allowed by the uplink data to be transmitted by the STA corresponding to the emergency identifier to the AP includes but is not limited to the followings:

Transmitting, by the STA, a second added control frame to the AP, wherein the second added control frame includes the maximum transmission delay allowed by the uplink data to be transmitted by the STA. Specifically, the STA carries the maximum transmission delay allowed by the uplink data to be transmitted by the STA via the added control frame to transmit the same to the AP. In order to facilitate a distinction from other added control frames, the added control frame carrying the maximum transmission delay allowed by the uplink data to be transmitted by the STA is referred to as the second added control frame herein.

Transmitting, by the STA, a second added management frame to the AP, wherein the second added management frame includes the maximum transmission delay allowed by the uplink data to be transmitted by the STA. Specifically, the STA carries the maximum transmission delay allowed by the uplink data to be transmitted by the STA via the added management frame to transmit the same to the AP. In order to facilitate a distinction from other added management frames, the added management frame carrying the maximum transmission delay allowed by the uplink data to be transmitted by the STA is referred to as the second added control frame herein.

Transmitting, by the STA, a second extended control frame to the AP, wherein the second extended control frame includes: the maximum transmission delay allowed by the uplink data to be transmitted by the STA. Specifically, the STA carries the maximum transmission delay allowed by the uplink data to be transmitted by the STA via the extended control frame by extending the existing control frame to transmit the same to the AP. For instance, the extended control frame herein may be a ps-poll frame. A manner for extending the control frame may be adding a field or an IE in the control frame to carry the maximum transmission delay allowed by the uplink data to be transmitted by the STA via the added field or the IE. In order to facilitate a distinction from other extended control frames, the extended control frame carrying the maximum transmission delay allowed by the uplink data to be transmitted by the STA is referred to as the second extended control frame herein.

Transmitting, by the STA, a second extended management frame to the AP, wherein the second extended management frame includes: the maximum transmission delay allowed by the uplink data to be transmitted by the STA. Specifically, the STA carries the maximum transmission delay allowed by the uplink data to be transmitted by the STA via the extended management frame by extending the existing management frame to transmit the same to the AP. A manner for extending the management frame may be adding a field or an IE in the management frame to carry the maximum transmission delay allowed by the uplink data to be transmitted by the STA via the added field or the IE. In order to facilitate a distinction from other extended management frames, the extended management frame carrying the maximum transmission delay allowed by the uplink data to be transmitted by the STA is referred to as the second extended management frame herein.

Transmitting, by the STA, a second extended data frame to the AP, wherein the second extended data frame includes: the maximum transmission delay allowed by the uplink data to be transmitted by the STA. Specifically, the STA carries the maximum transmission delay allowed by the uplink data to be transmitted by the STA via the extended data frame by extending the existing data frame to transmit the same to the AP. A manner for extending the data frame may be adding a field or an IE in the data frame to carry the maximum transmission delay allowed by the uplink data to be transmitted by the STA via the added field or the IE. In order to facilitate a distinction from other extended data frames, the extended data frame carrying the maximum transmission delay allowed by the uplink data to be transmitted by the STA is referred to as the second extended data frame herein.

Figure 3:
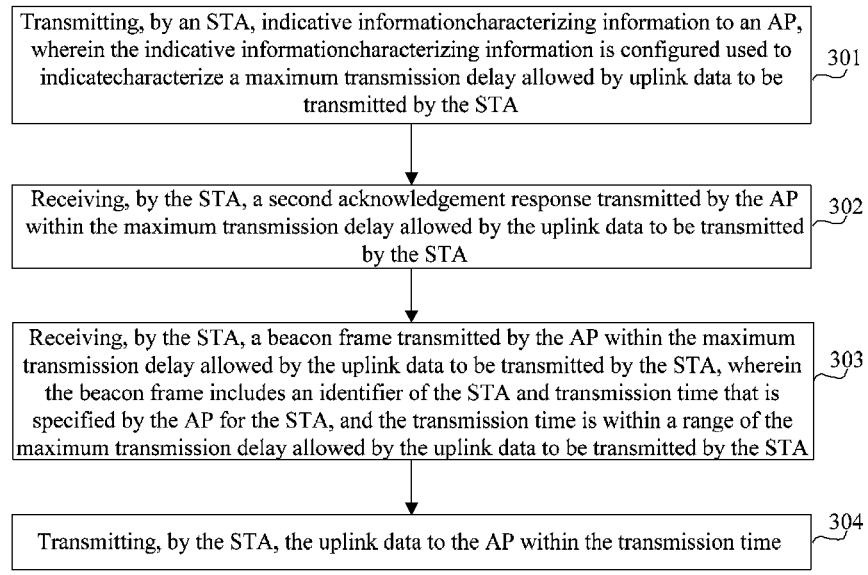
FIG. 3 is a flow chart of a method for transmitting data according to still another embodiment of the present invention.

FIG. 3 is a flow chart of a method for transmitting data according to still another embodiment of the present invention. As shown in FIG. 3, the method of this embodiment includes:

Step 301, transmitting, by an STA, characterizing information to an AP, wherein the characterizing information is used to characterize a maximum transmission delay allowed by uplink data to be transmitted by the STA.

For step 301, reference may be made to descriptions in step 101, which will not be repeated herein.

Step 302, receiving, by the STA, a second acknowledgement response transmitted by the AP within the maximum transmission delay allowed by the uplink data to be transmitted by the STA.

Step 303, receiving, by the STA, a beacon frame transmitted by the AP within the maximum transmission delay allowed by the uplink data to be transmitted by the STA, wherein the beacon frame includes an identifier of the STA and transmission time that is specified by the AP for the STA, and the transmission time is within a range of the maximum transmission delay allowed by the uplink data to be transmitted by the STA.

In this embodiment, after receiving characterizing information transmitted by the STA, the AP firstly returns the second acknowledgement response to the STA within the maximum transmission delay allowed by uplink data to be transmitted by the STA to inform the STA that the characterizing information is received. Correspondingly, the STA firstly receives the second acknowledgement response transmitted by the AP. The second acknowledgement response herein is also an ACK frame actually; however, different from the first acknowledgement response carrying the transmission time as described above, the second acknowledgement response herein does not carry the described transmission time, and is only used to inform the STA that the AP receives the characterizing information. After transmitting the second acknowledgement response to the STA, the AP transmits the beacon frame to the STA within the maximum transmission delay allowed by the uplink data to be transmitted by the STA to carry the transmission time that is specified for the STA via the beacon frame. Correspondingly, after receiving the second acknowledgement response, the STA receives the beacon frame which carries the transmission time that is specified by the AP for the STA and is transmitted by the AP.

For other descriptions related to step 303, reference may be made to embodiments described above, which will not be repeated herein.

Step 304, transmitting, by the STA, the uplink data to the AP within the transmission time.

For step 304, reference may be made to descriptions in step 103 as described above, which will not be repeated herein.

As seen above, in the method for transmitting data provided by this embodiment, an STA informs an AP that uplink data to be transmitted belong to emergency data by transmitting characterizing information that characterizes a maximum transmission delay allowed by the uplink data to be transmitted by the STA to the AP, so that the AP returns transmission time that is specified by the AP for the STA within a range of the maximum transmission delay to the STA within the maximum transmission delay, and after receiving the transmission time specified by the AP for the STA within the range of the maximum transmission delay, the STA transmits the uplink data to the AP within the transmission time, so that the uplink data are transmitted to the AP within the maximum transmission delay as far as possible, which is particularly applicable to data transmission in an emergency application scenario, and helps to guarantee requirements placed by emergency data upon the transmission delay.

Figure 4:
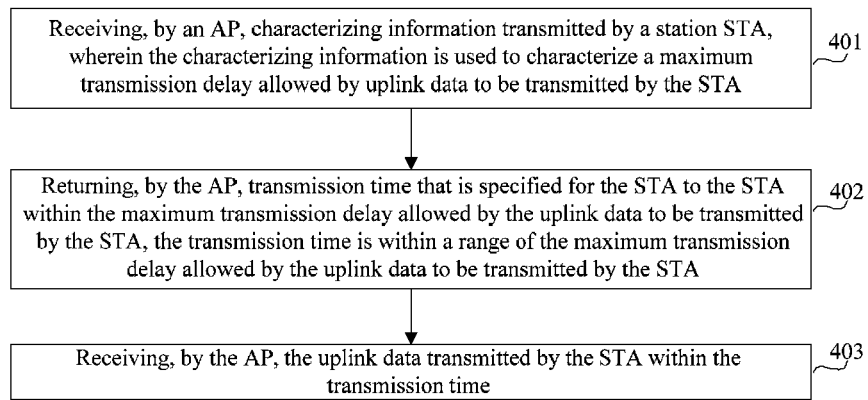
FIG. 4 is a flow chart of a method for receiving data according to an embodiment of the present invention.

FIG. 4 is a flow chart of a method for receiving data according to an embodiment of the present invention. As shown in FIG. 4, the method of this embodiment includes:

Step 401, receiving, by an AP, characterizing information transmitted by a station STA, wherein the characterizing information is used to characterize a maximum transmission delay allowed by uplink data to be transmitted by the STA.

Step 402, returning, by the AP, transmission time that is specified for the STA to the STA within the maximum transmission delay allowed by the uplink data to be transmitted by the STA, wherein the transmission time is within a range of the maximum transmission delay allowed by the uplink data to be transmitted by the STA.

Step 403, receiving, by the AP, the uplink data transmitted by the STA within the transmission time.

For descriptions on the STA in this embodiment, reference may be made to embodiments as shown in FIG. 1, which will not be repeated herein.

In this embodiment, the maximum transmission delay allowed by the uplink data to be transmitted by the STA actually refers to a period of time after the STA starts to transmit the characterizing information to the AP, and the STA needs to complete transmission of the uplink data to be transmitted during this period of time.

Before receiving the uplink data transmitted by the STA, the AP receives characterizing information that characterizes the maximum transmission delay allowed by the uplink data to be transmitted by the STA and is transmitted by the STA firstly. After receiving the characterizing information, the AP may learn that the uplink data to be transmitted by the STA is relatively urgent via the maximum transmission delay characterized by the characterizing information, based on this, the AP will schedule the STA promptly, so that the STA can transmit the uplink data to the AP within the maximum transmission delay allowed by the uplink data to be transmitted.

Subsequently, in order to enable the STA to transmit the uplink data to the AP within the maximum transmission delay allowed by the uplink data to be transmitted, the AP specifies transmission time within a range of the maximum transmission delay allowed by the uplink data to be transmitted by the STA for the STA within the maximum transmission delay allowed by the uplink data to be transmitted by the STA, and transmits the transmission time specified for the STA to the STA within the maximum transmission delay allowed by the uplink data to be transmitted by the STA. Wherein, the transmission time specified by the AP for the STA may be a time point, and may also be a time window (i.e. a short time).

Then, the AP receives the uplink data transmitted by the STA within the transmission time.

As seen above, in the method for receiving data provided by this embodiment, after receiving characterizing information that characterizes a maximum transmission delay allowed by uplink data to be transmitted by an STA and is transmitted by the STA, an AP returns transmission time that is specified for the STA within a range of the maximum transmission delay to the STA within the maximum transmission delay, and then receives the uplink data transmitted by the STA within the transmission time, so that the uplink data of the STA are transmitted to the AP within the maximum transmission delay as far as possible, which is particularly applicable to data transmission in an emergency application scenario, and helps to guarantee requirements placed by emergency data upon the transmission delay.

In an optional implementation, step 401, i.e. a way for the AP to receive the characterizing information transmitted by the STA includes but is not limited to the followings:

Receiving, by the AP, a first added control frame transmitted by the STA, wherein the first added control frame includes the characterizing information.

Receiving, by the AP, a first added management frame transmitted by the STA, wherein the first added management frame includes the characterizing information.

Receiving, by the AP, a first extended control frame transmitted by the STA, wherein the first extended control frame includes the characterizing information.

Receiving, by the AP, a first extended management frame transmitted by the STA, wherein the first added management frame includes the characterizing information.

Receiving, by the AP, a first extended data frame transmitted by the STA, wherein the first extended data frame includes the characterizing information.

For detailed descriptions of the above manners, reference may be made to descriptions in embodiments of the method for transmitting data as described above, which will not be repeated herein.

In an optional implementation, step 402, i.e. an implementation for the AP to return the transmission time that is specified for the STA to the STA within the maximum transmission delay allowed by the uplink data to be transmitted by the STA may include: transmitting, by the AP, a first acknowledgement response to the STA within the maximum transmission delay allowed by the uplink data to be transmitted by the STA, wherein the first acknowledgement response includes the specified time. For this implementation, reference may be made to descriptions in an optional implementation of step 102, which will not be repeated herein.

In an optional implementation, step 402, i.e. another implementation for the AP to return the transmission time that is specified for the STA to the STA within the maximum transmission delay allowed by the uplink data to be transmitted by the STA may include: transmitting, by the AP, a beacon frame to the STA within the maximum transmission delay allowed by the uplink data to be transmitted by the STA, wherein the beacon frame includes an identifier of the STA and the specified time. For this implementation, reference may be made to descriptions in another optional implementation of step 102, which will not be repeated herein.

Optionally, in this implementation, the beacon frame may also include: identifiers of other STAs besides the STA in step 401 and the transmission time that is specified by the AP for the other STAs within a range of the maximum transmission delay allowed by the uplink data to be transmitted by the other STAs. For detailed descriptions of this implementation, reference may be made to related descriptions in another optional implementation of step 102, which will not be repeated herein.

In an optional implementation, the characterizing information may be the maximum transmission delay allowed by the uplink data to be transmitted by the STA. The STA may support maximum transmission delays allowed by different uplink data being different by means of directly transmitting the characterizing information that characterizes the maximum transmission delay allowed by the uplink data to be transmitted to the AP, which has strong flexibility and adaptability.

Figure 5:
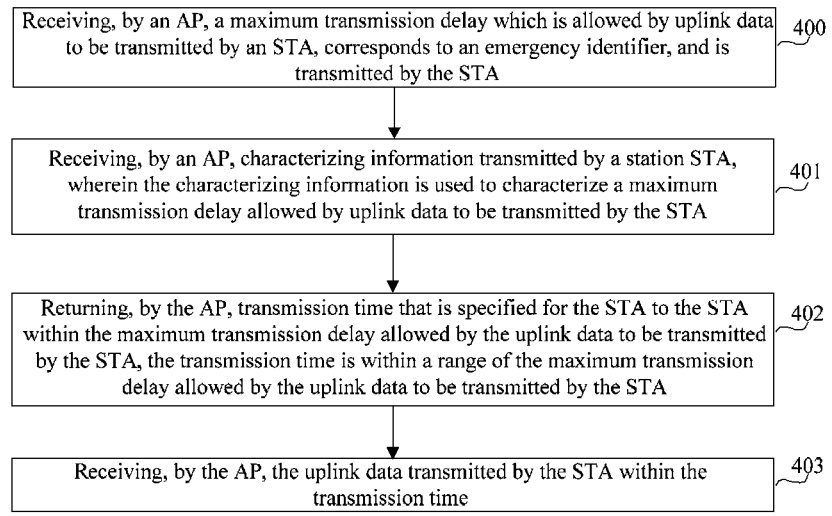
FIG. 5 is a flow chart of a method for receiving data according to another embodiment of the present invention.

In an optional implementation, the characterizing information may be an emergency identifier that identifies the uplink data to be transmitted by the STA as emergency data. Based on this, as shown in FIG. 5, the method of this embodiment before step 401 includes:

Step 400, receiving, by an AP, a maximum transmission delay which is allowed by uplink data to be transmitted by an STA, corresponds to an emergency identifier, and is transmitted by the STA.

Wherein, a manner for the AP to receive the maximum transmission delay allowed by the uplink data to be transmitted by the STA which corresponds to the emergency identifier and is transmitted by the STA includes but is not limited to the followings:

Receiving, by the AP, a second added control frame transmitted by the STA, wherein the second added control frame includes: the maximum transmission delay allowed by the uplink data to be transmitted by the STA.

Receiving, by the AP, a second added management frame transmitted by the STA, wherein the second added management frame includes: the maximum transmission delay allowed by the uplink data to be transmitted by the STA.

Receiving, by the AP, a second extended control frame transmitted by the STA, wherein the second extended control frame includes: the maximum transmission delay allowed by the uplink data to be transmitted by the STA.

Receiving, by the AP, a second extended management frame transmitted by the STA, wherein the second extended management frame includes: the maximum transmission delay allowed by the uplink data to be transmitted by the STA.

Receiving, by the AP, a second extended data frame transmitted by the STA, wherein the second extended data frame includes: the maximum transmission delay allowed by the uplink data to be transmitted by the STA.

For step 400 and detailed descriptions of the manners as described above, reference may be made to embodiments as shown in FIG. 3, which will not be repeated herein.

Figure 6:
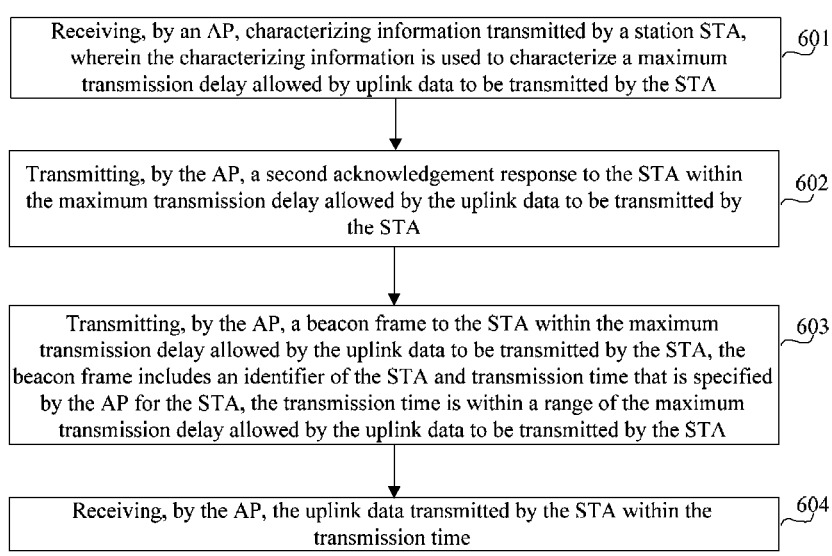
FIG. 6 is a flow chart of a method for receiving data according to still another embodiment of the present invention.

FIG. 6 is a flow chart of a method for receiving data according to still another embodiment of the present invention. As shown in FIG. 6, the method of this embodiment includes:

Step 601, receiving, by an AP, characterizing information transmitted by a station STA, wherein the characterizing information is used to characterize a maximum transmission delay allowed by uplink data to be transmitted by the STA.

For step 601, reference may be made to descriptions in step 401, which will not be repeated herein.

Step 602, transmitting, by the AP, a second acknowledgement response to the STA within the maximum transmission delay allowed by the uplink data to be transmitted by the STA.

Step 603, transmitting, by the AP, a beacon frame to the STA within the maximum transmission delay allowed by the uplink data to be transmitted by the STA, wherein the beacon frame includes an identifier of the STA and transmission time that is specified by the AP for the STA, the transmission time is within a range of the maximum transmission delay allowed by the uplink data to be transmitted by the STA.

In this embodiment, after receiving characterizing information transmitted by an STA, an AP firstly returns a second acknowledgement response to the STA within a maximum transmission delay allowed by uplink data to be transmitted by the STA to inform the STA that the characterizing information is received. The second acknowledgement response herein is also an ACK frame actually; however, different from the first acknowledgement response carrying the transmission time as described above, the second acknowledgement response herein does not carry the described transmission time, and is only used to inform the STA that the AP receives the characterizing information. After transmitting the second acknowledgement response to the STA, the AP transmits a beacon frame to the STA within the maximum transmission delay allowed by the uplink data to be transmitted by the STA to carry the transmission time that is specified for the STA via the beacon frame.

Step 604, receiving, by the AP, the uplink data transmitted by the STA within the transmission time.

For step 604, reference may be made to descriptions in step 403 as described above, which will not be repeated herein.

As seen above, in the method for receiving data provided by this embodiment, after receiving characterizing information that characterizes a maximum transmission delay allowed by uplink data to be transmitted by an STA and is transmitted by the STA, an AP returns transmission time that is specified for the STA within a range of the maximum transmission delay to the STA within the maximum transmission delay, and then receives the uplink data transmitted by the STA within the transmission time, so that the uplink data of the STA are transmitted to the AP within the maximum transmission delay as far as possible, which is particularly applicable to data transmission in an emergency application scenario, and helps to guarantee requirements placed by emergency data upon the transmission delay.

Figure 7:
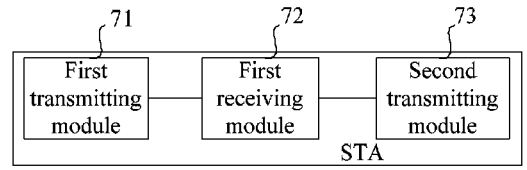
FIG. 7 is a schematic structural diagram of an STA according to an embodiment of the present invention.

FIG. 7 is a schematic structural diagram of an STA according to an embodiment of the present invention. As shown in FIG. 7, the STA of this embodiment includes: a first transmitting module 71, a first receiving module 72 and a second transmitting module 73.

The first transmitting module 71 is configured to transmit characterizing information to an AP, wherein the characterizing information is used to characterize a maximum transmission delay allowed by uplink data to be transmitted by the STA in this embodiment.

The first receiving module 72 is configured to receive transmission time that is specified for the STA in this embodiment and is returned by the AP within the maximum transmission delay allowed by the uplink data to be transmitted by the STA, wherein the transmission time is within a range of the maximum transmission delay allowed by the uplink data to be transmitted by the STA in this embodiment. Optionally, the first receiving module 72 is connected with the first transmitting module 71, and is configured to receive the transmission time returned by the AP after the first transmitting module 71 transmits the characterizing information to the AP. The first receiving module 72 is also connected with the second transmitting module 73, and is configured to provide the transmission time to the second transmitting module 73.

The second transmitting module 73 is configured to transmit the uplink data to the AP within the transmission time received by the first receiving module 72.

In an optional implementation, the first receiving module 72 may be specifically configured to receive a first acknowledgement response transmitted by the AP within the maximum transmission delay allowed by the uplink data to be transmitted by the STA in this embodiment, wherein the first acknowledgement response includes the specified time.

In an optional implementation, the first receiving module 72 may be specifically configured to receive a beacon frame transmitted by the AP within the maximum transmission delay allowed by the uplink data to be transmitted by the STA in this embodiment, wherein the beacon frame includes an identifier of the STA in this embodiment and the transmission time.

Optionally, in addition to the identifier of the STA in this embodiment and the transmission time corresponding to the STA in this embodiment, the beacon frame may also include: identifiers of other STAs besides the STA in this embodiment and transmission time that is specified by the AP for the other STAs within a range of the maximum transmission delay allowed by the uplink data to be transmitted by the other STAs.

Figure 8:
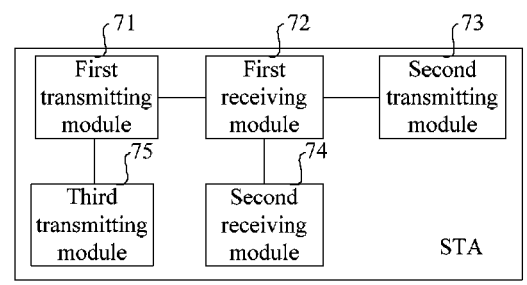
FIG. 8 is a schematic structural diagram of an STA according to another embodiment of the present invention.

In an optional implementation, as shown in FIG. 8, the STA of this embodiment also includes: a second receiving module 74. The second receiving module 74 is connected with the first receiving module 72, and is configured to receive a second acknowledgement response transmitted by the AP within the maximum transmission delay allowed by the uplink data to be transmitted by the STA in this embodiment before the first receiving module 72 receives the beacon frame.

In an optional implementation, the first transmitting module 71 may be specifically configured to transmit a first added control frame or a first added management frame to the AP, wherein the first added control frame or the first added management frame includes the characterizing information. Or, the first transmitting module 71 may be specifically configured to transmit a first extended control frame, a first extend management frame or a first extended data frame to the AP, wherein the first extended control frame, the first extended management frame or the first extended data frame includes the characterizing information.

In an optional implementation, the characterizing information transmitted by the STA in this embodiment to the AP may be the maximum transmission delay allowed by the uplink data to be transmitted by the STA in this embodiment.

In an optional implementation, the characterizing information transmitted by the STA in this embodiment to the AP may be an emergency identifier that identifies the uplink data to be transmitted by the STA in this embodiment as emergency data. Based on this, as shown in FIG. 8, the STA of this embodiment may also include: a third transmitting module 75.

The third transmitting module 75 is connected with the first transmitting module 71, and is configured to transmit the maximum transmission delay allowed by the uplink data to be transmitted by the STA in this embodiment corresponding to the emergency identifier to the AP before the first transmitting module 71 transmits the characterizing information to the AP, so that the AP determines the maximum transmission delay allowed by the uplink data to be transmitted by the STA in this embodiment according to the emergency identifier.

Optionally, the third transmitting module 75 may be specifically configured to transmit a second added control frame or a second added management frame to the AP, wherein the second added control frame or the second added management frame includes: the maximum transmission delay allowed by the uplink data to be transmitted by the STA in this embodiment. Or, the third transmitting module 75 may be specifically configured to transmit a second extended control frame, a second extended management frame or a second extended data frame to the AP, wherein the second extended control frame, the second extended management frame or the second extended data frame includes: the maximum transmission delay allowed by the uplink data to be transmitted by the STA in this embodiment.

Each functional module of the STA according to this embodiment may be configured to perform a corresponding process in embodiments of the method for transmitting data described above, and specific operating principles thereof will not be repeated herein, reference may be made to descriptions of the method embodiments for details.

In this embodiment, an STA informs an AP that uplink data to be transmitted belong to emergency data by transmitting characterizing information that characterizes a maximum transmission delay allowed by the uplink data to be transmitted by the STA to the AP, so that the AP returns transmission time that is specified for the STA within a range of the maximum transmission delay to the STA within the maximum transmission delay, after receiving the transmission time specified by the AP for the STA within the range of the maximum transmission delay, the STA transmits the uplink data to the AP within the transmission time, so that the uplink data are transmitted to the AP within the maximum transmission delay as far as possible, which is particularly applicable to data transmission in an emergency application scenario, and helps to guarantee requirements placed by emergency data upon the transmission delay.

Figure 9:
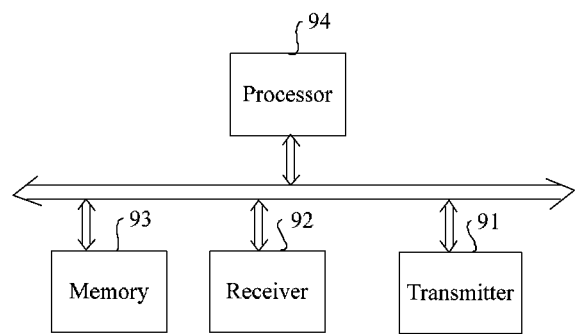
FIG. 9 is a schematic structural diagram of an STA according to still another embodiment of the present invention.

FIG. 9 is a schematic structural diagram of an STA according to still another embodiment of the present invention. As shown in FIG. 9, the STA of this embodiment includes: a transmitter 91, a receiver 92, a memory 93 and a bus. The transmitter 91, the receiver 92 and the memory 93 are connected to each other via the bus, and complete communications therebetween. The bus may be an industry standard architecture (Industry Standard Architecture, ISA for short) bus, a peripheral component interconnect (Peripheral Component Interconnect, PCI for short) bus or an extended industry standard architecture (Extended Industry Standard Architecture, EISA for short) bus. The bus may be divided into an address bus, a data bus, a control bus, etc. For the sake of convenience, only a bold line is shown in FIG. 9, but it does not mean that there is only a bus or a type of bus.

The transmitter 91 is configured to: transmit characterizing information to an AP, wherein the characterizing information is used to characterize a maximum transmission delay allowed by uplink data to be transmitted by the STA in this embodiment; and after the receiver 92 receives transmission time returned by the AP, transmit the uplink data to the AP within the transmission time.

The receiver 92 is configured to receive transmission time that is specified for the STA in this embodiment and returned by the AP within the maximum transmission delay allowed by the uplink data to be transmitted by the STA in this embodiment after the transmitter 91 transmits the characterizing information to the AP, wherein the transmission time is within a range of the maximum transmission delay allowed by the uplink data to be transmitted by the STA in this embodiment.

Besides having the functions described above, the transmitter 91 and the receiver 92 may also complete communications between the STA of this embodiment and any other devices.

The memory 93 is configured to store the transmission time received by the receiver 92 and the uplink data to be transmitted by the transmitter 91. Additionally, the memory 93 may also store a program. Specifically, the program may include a program code, and the program code includes computer operating instructions. The memory 93 may include a high-speed RAM memory, and may also include a non-volatile memory (non-volatile memory), such as at least one disk memory.

Furthermore, the STA of this embodiment may also include a processor 94. The processor 94 may be configured to run the program stored in the memory 93 so as to implement corresponding functions. The processor 94 may be a central processing unit (Central Processing Unit, CPU for short), or an application specific integrated circuit (Application Specific Integrated Circuit, ASIC for short), or one or more integrated circuits configured for implementing embodiments of the present invention.

The STA according to this embodiment may be configured to perform corresponding processes in embodiments of the method for transmitting data as described above, and specific operating principles thereof will not be repeated herein, reference may be made to descriptions of the method embodiments for details.

In this embodiment, an STA informs an AP that uplink data to be transmitted belong to emergency data by transmitting characterizing information that characterizes a maximum transmission delay allowed by the uplink data to be transmitted by the STA to the AP, so that the AP returns transmission time that is specified for the STA within a range of the maximum transmission delay to the STA within the maximum transmission delay, after receiving the transmission time specified by the AP for the STA within the range of the maximum transmission delay, the STA transmits the uplink data to the AP within the transmission time, so that the uplink data are transmitted to the AP within the maximum transmission delay as far as possible, which is particularly applicable to data transmission in an emergency application scenario, and helps to guarantee requirements placed by emergency data upon the transmission delay.

Figure 10:
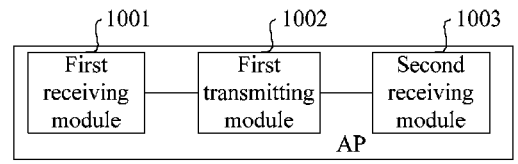
FIG. 10 is a schematic structural diagram of an AP according to an embodiment of the present invention.

FIG. 10 is a schematic structural diagram of an AP according to an embodiment of the present invention. As shown in FIG. 10, the AP of this embodiment includes: a first receiving module 1001, a first transmitting module 1002 and a second receiving module 1003.

The first receiving module 1001 is configured to receive characterizing information transmitted by an STA, wherein the characterizing information is used to characterize a maximum transmission delay allowed by uplink data to be transmitted by the STA. The first receiving module 1001 is connected with the first transmitting module 1002, and is configured to provide the first transmitting module 1002 with the maximum transmission delay allowed by the uplink data to be transmitted by the STA.

The first transmitting module 1002 is configured to return transmission time that is specified for the STA to the STA within the maximum transmission delay allowed by the uplink data to be transmitted by the STA, wherein the transmission time is within a range of the maximum transmission delay allowed by the uplink data to be transmitted by the STA. The first transmitting module 1002 is connected with the second receiving module 1003, and may be configured to provide the transmission time to the second receiving module 1003.

The second receiving module 1003 is configured to receive the uplink data transmitted by the STA within the transmission time.

In an optional implementation, the first transmitting module 1002 may be specifically configured to transmit a first acknowledgement response to the STA within the maximum transmission delay allowed by the uplink data to be transmitted by the STA, wherein the first acknowledgement response includes the specified time.

In an optional implementation, the first transmitting module 1002 may be specifically configured to transmit a beacon frame to the STA within the maximum transmission delay allowed by the uplink data to be transmitted by the STA, wherein the beacon frame includes an identifier of the STA and the specified time.

Optionally, in addition to the identifier of the STA and the transmission time, the beacon frame also includes: identifiers of other STAs besides the STA and transmission time that is specified by the AP for the other STAs within a range of the maximum transmission delay allowed by the uplink data to be transmitted by the other STAs.

Figure 11:
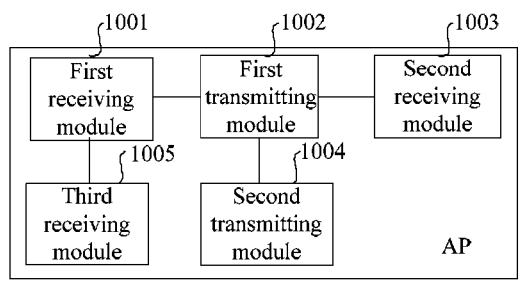
FIG. 11 is a schematic structural diagram of an AP according to another embodiment of the present invention.

In an optional implementation, as shown in FIG. 11, the AP of this embodiment also includes: a second transmitting module 1004. The second transmitting module 1004 is connected with the first transmitting module 1002, and is configured to transmit a second acknowledgement response to the STA within the maximum transmission delay allowed by the uplink data to be transmitted by the STA before the first transmitting module 1002 transmits the beacon frame to the STA.

In an optional implementation, the first receiving module 1001 may be specifically configured to receive a first added control frame or a first added management frame transmitted by the STA, wherein the first added control frame or the first added management frame includes the characterizing information. Or, the first receiving module 1001 may be specifically configured to receive a first extended control frame, a first extend management frame or a first extended data frame transmitted by the STA, wherein the first extended control frame, the first extended management frame or the first extended data frame includes the characterizing information.

In an optional implementation, the characterizing information may be the maximum transmission delay allowed by the uplink data to be transmitted by the STA.

In an optional implementation, the characterizing information may be an emergency identifier that identifies the uplink data to be transmitted by the STA as emergency data. Based on this, as shown in FIG. 11, the AP of this embodiment may also include a third receiving module 1005.

The third receiving module 1005 is connected with the first receiving module 1001, and is configured to receive the maximum transmission delay which is allowed by the uplink data to be transmitted by the STA, corresponds to the emergency identifier, and is transmitted by the STA, before the first receiving module 1001 receives the characterizing information.

In an optional implementation, the third receiving module 1005 may be specifically configured to receive a second added control frame or a second added management frame transmitted by the STA, wherein the second added control frame or the second added management frame includes: the maximum transmission delay allowed by the uplink data to be transmitted by the STA. Or, the third receiving module 1005 may be specifically configured to receive a second extended control frame, a second extended management frame or a second extended data frame transmitted by the STA, wherein the second extended control frame, the second extended management frame or the second extended data frame includes: the maximum transmission delay allowed by the uplink data to be transmitted by the STA.

Each functional module of the AP according to this embodiment may be configured to perform corresponding processes in embodiments of the method for receiving data described above, and specific operating principles thereof will not be repeated herein, reference may be made to descriptions of the method embodiments for details.

In this embodiment, after receiving characterizing information that characterizes a maximum transmission delay allowed by uplink data to be transmitted by an STA and is transmitted by the STA, an AP returns transmission time that is specified for the STA within a range of the maximum transmission delay to the STA within the maximum transmission delay, and then receives the uplink data transmitted by the STA within the transmission time, so that the uplink data of the STA are transmitted to the AP within the maximum transmission delay as far as possible, which is particularly applicable to data transmission in an emergency application scenario, and helps to guarantee requirements placed by emergency data upon the transmission delay.

Figure 12:
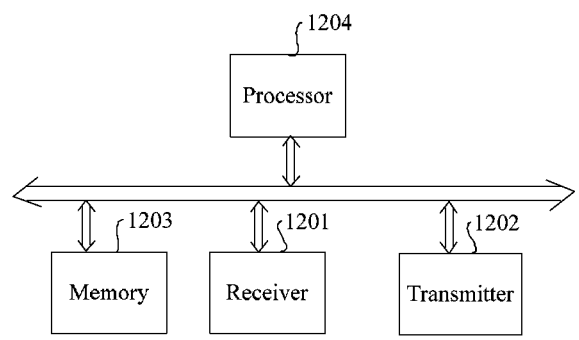
FIG. 12 is a schematic structural diagram of an AP according to still another embodiment of the present invention.

FIG. 12 is a schematic structural diagram of an AP according to still another embodiment of the present invention. As shown in FIG. 12, the AP of this embodiment includes: a receiver 1201, a transmitter 1202, a memory 1203 and a bus. The receiver 1201, the transmitter 1202, and the memory 1203 are connected to each other via the bus, and complete communications therebetween. The bus may be an ISA bus, a PCI bus or an EISA bus, etc. The bus may be divided into an address bus, a data bus, a control bus, etc. For the sake of convenience, only a bold line is shown in FIG. 12, but it does not mean that there is only a bus or a type of bus.

The receiver 1201 is configured to: receive characterizing information transmitted by an STA, wherein the characterizing information is configured to characterize a maximum transmission delay allowed by uplink data to be transmitted by the STA; and after the transmitter 1202 returns transmission time that is specified for the STA to the STA, receive the uplink data transmitted by the STA within the transmission time.

The transmitter 1202 is configured to return transmission time that is specified for the STA to the STA within the maximum transmission delay allowed by the uplink data to be transmitted by the STA after the receiver 1201 receives the characterizing information transmitted by the STA, wherein the transmission time is within a range of the maximum transmission delay allowed by the uplink data to be transmitted by the STA.

Besides having the functions described above, the transmitter 1202 and the receiver 1201 may also complete communication between the AP of this embodiment and any other devices.

The memory 1203 is configured to store the characterizing information and the uplink data received by the receiver 1201, and temporarily store the transmission time transmitted by the transmitter 1202. Additionally, the memory 1203 may also store a program. Specifically, the program may include a program code, and the program code includes computer operating instructions. The memory 1203 may include a high-speed RAM memory, and may also include a non-volatile memory (non-volatile memory), such as at least one disk memory.

Furthermore, the AP of this embodiment may also include a processor 1204. The processor 1204 may be configured to run the program stored in the memory 1203 so as to implement corresponding functions. The processor 1204 may be a CPU, or an ASIC, or one or more integrated circuits configured for implementing embodiments of the present invention.

The AP according to this embodiment may be configured to perform corresponding processes in embodiments of the method for receiving data as described above, and specific operating principles thereof will not be repeated herein, reference may be made to descriptions of the method embodiments for details.

In this embodiment, after receiving characterizing information that characterizes a maximum transmission delay allowed by uplink data to be transmitted by an STA and is transmitted by the STA, an AP returns transmission time that is specified for the STA within a range of the maximum transmission delay to the STA within the maximum transmission delay, and then receives the uplink data transmitted by the STA within the transmission time, so that the uplink data of the STA are transmitted to the AP within the maximum transmission delay as far as possible, which is particularly applicable to data transmission in an emergency application scenario, and helps to guarantee transmission requirements placed by emergency data upon the transmission delay.

Persons of ordinary skill in the art may understand that, all or a part of the steps of the foregoing method embodiments may be implemented by a program instructing relevant hardware. The foregoing program may be stored in a computer readable storage medium. When the program runs, the steps of the foregoing method embodiments are performed. The foregoing storage medium includes various media capable of storing program codes, such as an ROM, an RAM, a magnetic disk, or an optical disc.

Finally, it should be noted that the foregoing embodiments are merely intended for describing the technical solutions of the present invention rather than limiting the present invention. Although the present invention is described in detail with reference to the foregoing embodiments, persons of ordinary skill in the art should understand that they may still make modifications to the technical solutions described in the foregoing embodiments, or make equivalent replacements to some or all technical features therein; however, these modifications or replacements do not make the essence of corresponding technical solutions depart from the scope of the technical solutions in the embodiments of the present invention.

What is claimed is:

1. A method for transmitting data, the method comprising:
transmitting, by a station (STA) to a radio access point (AP), characterizing information, including an emergency identifier that identifies uplink data to be transmitted by the STA as emergency data, used to characterize a maximum transmission delay allowed for uplink data to be transmitted by the STA;
receiving, by the STA, transmission time specified for the STA and returned by the AP within the maximum transmission delay allowed for the uplink data to be transmitted by the STA, wherein the transmission time is within a range of the maximum transmission delay allowed for the uplink data to be transmitted by the STA; and
transmitting, by the STA, the uplink data to the AP within the transmission time.

2. The method for transmitting data according to claim 1, wherein, receiving, by the STA, the transmission time specified for the STA and returned by the AP within the maximum transmission delay allowed for the uplink data to be transmitted by the STA comprises:
receiving, by the STA, a first acknowledgement response transmitted by the AP within the maximum transmission delay allowed for the uplink data to be transmitted by the STA, wherein the first acknowledgement response comprises the specified transmission time.

3. The method for transmitting data according to claim 1, wherein, receiving, by the STA, the transmission time specified for the STA and returned by the AP within the maximum transmission delay allowed for the uplink data to be transmitted by the STA comprises:
receiving, by the STA, a beacon frame transmitted by the AP within the maximum transmission delay allowed for the uplink data to be transmitted by the STA, wherein the beacon frame comprises an identifier of the STA and of the transmission time.

4. The method for transmitting data according to claim 1, wherein, transmitting, by the STA, the characterizing information to the radio access point AP comprises:
transmitting, by the STA to the AP, one of a first added control frame, a first added management frame, a first extended control frame, a first extend management frame and a first extended data frame, wherein the first added control frame, the first added management frame, the first extended control frame, the first extended management frame, or the first extended data frame comprises the characterizing information.

5. The method for transmitting data according to claim 1, wherein before transmitting, by the station STA, the characterizing information to the radio access point AP, the method further comprises:
transmitting, by the STA to the AP, the maximum transmission delay allowed for the uplink data to be transmitted by the STA and which corresponds to the emergency identifier, so that the AP determines the maximum transmission delay allowed for the uplink data to be transmitted by the STA according to the emergency identifier.

6. The method for transmitting data according to claim 5, wherein, transmitting, by the STA to the AP, the maximum transmission delay allowed for the uplink data to be transmitted by the STA and which corresponds to the emergency identifier, comprises:
transmitting, by the STA to the AP, one of a second added control frame, a second added management frame, a second extended control frame, a second extended management frame, and a second extended data frame, wherein the second added control frame, the second added management frame, the second extended control frame, the second extended management frame, or the second extended data frame comprises: the maximum transmission delay allowed for the uplink data to be transmitted by the STA.

7. A method for receiving data, the method comprising:
receiving, by a radio access point (AP), characterizing information, including an emergency identifier that identifies uplink data to be transmitted by the STA as emergency data, transmitted by a station (STA), and used to characterize a maximum transmission delay allowed for uplink data to be transmitted by the STA;
maintaining, by the AP, a corresponding relation between the emergency identifier sent by the STA and the maximum transmission delay allowed for the emergency data on the STA;
returning, by the AP, transmission time specified for the STA to the STA within the maximum transmission delay allowed for the uplink data to be transmitted by the STA, wherein the transmission time is within a range of the maximum transmission delay allowed for the uplink data to be transmitted by the STA; and
receiving, by the AP, the uplink data transmitted by the STA within the transmission time.

8. The method for receiving data according to claim 7, wherein, returning, by the AP, the transmission time specified for the STA to the STA within the maximum transmission delay allowed for the uplink data to be transmitted by the STA comprises:
transmitting, by the AP, a first acknowledgement response to the STA within the maximum transmission delay allowed for the uplink data to be transmitted by the STA, wherein the first acknowledgement response includes the specified time.

9. The method for receiving data according to claim 7, wherein, returning, by the AP, the transmission time specified for the STA to the STA within the maximum transmission delay allowed for the uplink data to be transmitted by the STA comprises:
transmitting, by the AP, a beacon frame to the STA within the maximum transmission delay allowed for the uplink data to be transmitted by the STA, wherein the beacon frame includes an identifier of the STA and the specified time.

10. The method for receiving data according to claim 9, wherein, the beacon frame also includes: identifiers of other STAs besides the STA and transmission times specified by the AP for the other STAs within a range of the maximum transmission delay allowed for the uplink data to be transmitted by the other STAs.

11. The method for receiving data according to claim 7, wherein, receiving, by the AP, the characterizing information transmitted by the STA comprises:
receiving, by the AP, one of a first added control frame including the characterizing information, a first added management frame including the characterizing information, a first extended control frame including the characterizing information, a first extended management frame including the characterizing information, and a first extended data frame including the characterizing information transmitted by the STA.

12. The method for receiving data according to claim 7, wherein before receiving, by the AP, the characterizing information transmitted by the STA, the method further comprises:

receiving, by the AP, the maximum transmission delay allowed for the uplink data to be transmitted by the STA which corresponds to the emergency identifier and is transmitted by the STA.

13. The method for receiving data according to claim 12, wherein, receiving, by the AP, the maximum transmission delay allowed for the uplink data to be transmitted by the STA which corresponds to the emergency identifier and is transmitted by the STA comprises:
receiving, by the AP, one of a second added control frame including the maximum transmission delay allowed for the uplink data to be transmitted by the STA, a second added management frame including the maximum transmission delay allowed for the uplink data to be transmitted by the STA, a second extended control frame including the maximum transmission delay allowed for the uplink data to be transmitted by the STA, a second extended management frame including the maximum transmission delay allowed for the uplink data to be transmitted by the STA, and a second extended data frame transmitted by the STA and including the maximum transmission delay allowed for the uplink data to be transmitted by the STA.

14. A station (STA), comprising:
a processor; and
a non-transitory computer-readable storage medium including computer-executable instructions executed by the processor to perform, on the STA, the method comprising:
transmitting, to a radio access point (AP), characterizing information, including an emergency identifier that identifies uplink data to be transmitted by the STA as emergency data, used to characterize a maximum transmission delay allowed for uplink data to be transmitted by the STA;
receiving transmission time specified for the STA and returned by the AP within the maximum transmission delay allowed for the uplink data to be transmitted by the STA, wherein the transmission time is within a range of the maximum transmission delay allowed for the uplink data to be transmitted by the STA; and
transmitting the uplink data to the AP within the transmission time.

15. The STA according to claim 14 further comprising instructions for receiving a first acknowledgement response including the specified time and transmitted by the AP within the maximum transmission delay allowed for the uplink data to be transmitted by the STA.

16. The STA according to claim 14, further comprising instructions for receiving a beacon frame including an identifier of the STA and the transmission time and transmitted by the AP within the maximum transmission delay allowed for the uplink data to be transmitted by the STA.

17. The STA according to claim 14, further comprising instructions for
transmitting, to the AP, one of a first added control frame including the characterizing information, a first added management frame including the characterizing information, a first extended control frame including the characterizing information, a first extend management frame including the characterizing information, and a first extended data frame including the characterizing information.

18. The STA according to claim 14, further comprising instructions for transmitting, to the AP before the first transmitting module transmits the characterizing information to the AP, the maximum transmission delay allowed for the uplink data to be transmitted by the STA which corresponds to the emergency identifier, so that the AP determines the maximum transmission delay allowed for the uplink data to be transmitted by the STA according to the emergency identifier.

19. The STA according to claim 18, further comprising instructions for
transmitting, to the AP, one of a second added control frame including the maximum transmission delay allowed for the uplink data to be transmitted by the STA, a second added management frame including the maximum transmission delay allowed for the uplink data to be transmitted by the STA, a second extended control frame including the maximum transmission delay allowed for the uplink data to be transmitted by the STA, a second extended management frame including the maximum transmission delay allowed for the uplink data to be transmitted by the STA, and a second extended data frame including the maximum transmission delay allowed for the uplink data to be transmitted by the STA.

20. A radio access point AP, characterized by comprising:
a processor; and
a non-transitory computer-readable storage medium including computer-executable instructions executed by the processor to perform, on the STA, the method comprising:
receiving characterizing information, including an emergency identifier that identifies uplink data to be transmitted by the STA as emergency data, transmitted by a station (STA) and used to characterize a maximum transmission delay allowed for uplink data to be transmitted by the STA;
returning transmission time specified for the STA to the STA within the maximum transmission delay allowed for the uplink data to be transmitted by the STA, wherein the transmission time is within a range of the maximum transmission delay allowed for the uplink data to be transmitted by the STA; and
receiving the uplink data transmitted by the STA within the transmission time.

21. The AP according to claim 20, further comprising instructions for transmitting a first acknowledgement response including the specified time to the STA within the maximum transmission delay allowed for the uplink data to be transmitted by the STA.

22. The AP according to claim 20, further comprising instructions for transmitting a beacon frame including an identifier of the STA and the specified time to the STA within the maximum transmission delay allowed for the uplink data to be transmitted by the STA.

23. The AP according to claim 20, further comprising instructions for
receiving one of a first added control frame including the characterizing information, a first added management frame including the characterizing information transmitted by the STA, a first extended control frame including the characterizing information, a first extend management frame including the characterizing information, and a first extended data frame including the characterizing information transmitted by the STA.

24. The AP according to claim 20, further comprising instructions for
receiving, before the first receiving module receives the characterizing information, the maximum transmission delay allowed for the uplink data to be transmitted by the STA which corresponds to the emergency identifier and is transmitted by the STA.

25. The AP according to claim 24, further comprising instructions for
receiving one of a second added control frame including the maximum transmission delay allowed for the uplink data to be transmitted by the STA, a second added management frame including the maximum transmission delay allowed for the uplink data to be transmitted by the STA and transmitted by the STA, a second extended control frame including the maximum transmission delay allowed for the uplink data to be transmitted by the STA, a second extended management frame including the maximum transmission delay allowed for the uplink data to be transmitted by the STA, and a second extended data frame including the maximum transmission delay allowed for the uplink data to be transmitted by the STA and transmitted by the STA.

* * * * *